United States Patent
Zhao et al.

(10) Patent No.: US 12,379,434 B2
(45) Date of Patent: Aug. 5, 2025

(54) MAGNETIC RESONANCE SYSTEM WITH SPATIAL SELECTIVITY AND WORKING METHOD THEREOF

(71) Applicant: WUXI MARVEL STONE HEALTHCARE CO., LTD., Wuxi (CN)

(72) Inventors: Yue Zhao, Chengdu (CN); Hai Luo, Chengdu (CN); Chao Wang, Chengdu (CN); Yunhao Xie, Chengdu (CN); Jianxiong Hu, Chengdu (CN); Wenkui Hou, Chengdu (CN); Xiao Chen, Chengdu (CN); Min Wu, Chengdu (CN); Ziyue Wu, Chengdu (CN)

(73) Assignee: WUXI MARVEL STONE HEALTHCARE CO., LTD., Wuxi (CN)

( * ) Notice: Subject to any disclaimer, the term of this patent is extended or adjusted under 35 U.S.C. 154(b) by 0 days.

(21) Appl. No.: 19/091,913

(22) Filed: Mar. 27, 2025

(65) Prior Publication Data
US 2025/0224468 A1    Jul. 10, 2025

Related U.S. Application Data

(63) Continuation of application No. PCT/CN2022/130123, filed on Nov. 4, 2022.

(30) Foreign Application Priority Data

Oct. 9, 2022    (CN) .......................... 202211230051.4

(51) Int. Cl.
*G01V 3/00*        (2006.01)
*G01R 33/36*       (2006.01)
(Continued)

(52) U.S. Cl.
CPC ..... *G01R 33/3614* (2013.01); *G01R 33/3607* (2013.01); *G01R 33/4838* (2013.01); *G01R 33/5608* (2013.01)

(58) Field of Classification Search
CPC ............ G01R 33/3614; G01R 33/3607; G01R 33/4838; G01R 33/5608
(Continued)

(56) References Cited

U.S. PATENT DOCUMENTS

2008/0167548 A1    7/2008 Sorensen

FOREIGN PATENT DOCUMENTS

CN    101598775 A      12/2009
CN    105388435 A  *   3/2016   ......... G01R 33/3628
(Continued)

*Primary Examiner* — Walter L Lindsay, Jr.
*Assistant Examiner* — Frederick Wenderoth
(74) *Attorney, Agent, or Firm* — Bayramoglu Law Offices LLC

(57) ABSTRACT

The provided is a magnetic resonance (MR) system with spatial selectivity and a working method thereof. The MR system includes a data display and processing module, a spectrometer with at least one transmission channel, at least one power amplifier, a transmit-receive (TR) switch, a preamplifier, multiple sets of coils, and a magnet module, where when a number of transmission channels of the spectrometer is not less than a number of coils, one power amplifier is connected to the TR switch, while other power amplifiers are correspondingly connected to other coils (2, 3, 4) except for a main coil (1); when the number of the transmission channels of the spectrometer is less than the number of the coils, an output terminal of the at least one power amplifier is first connected to at least one power divider and multiple phase shifters and then connected to the coil.

20 Claims, 5 Drawing Sheets

(51) Int. Cl.
  *G01R 33/483* (2006.01)
  *G01R 33/56* (2006.01)

(58) Field of Classification Search
  USPC .......................................................... 324/318
  See application file for complete search history.

(56) References Cited

FOREIGN PATENT DOCUMENTS

| | | | |
|---|---|---|---|
| CN | 108827996 A | 11/2018 |
| CN | 114062412 A | 2/2022 |
| CN | 114720926 A | 7/2022 |
| CN | 114720927 A | 7/2022 |

\* cited by examiner

MAGNETIC RESONANCE SYSTEM WITH SPATIAL SELECTIVITY AND WORKING METHOD THEREOF

CROSS-REFERENCE TO THE RELATED APPLICATIONS

This application is a continuation application of International Application No. PCT/CN2022/130123, filed on Nov. 4, 2022, which is based upon and claims priority to Chinese Patent Application No. 202211230051.4, filed on Oct. 9, 2022, the entire contents of which are incorporated herein by reference.

TECHNICAL FIELD

The present disclosure belongs to the technical field of magnetic resonance (MR), and in particular relates to an MR system with spatial selectivity and a working method thereof.

BACKGROUND

Generally, when magnetic resonance (MR) testing is performed using a unilateral magnet MR system, the acquired signals are often mixed signals from various tissues due to the lack of a gradient system capable of spatial encoding. Consequently, the analysis of the pathological condition of a specific tissue is likely to be interfered with signals from surrounding tissues, thereby leading to testing errors. MR systems with spatial selectivity can remove signals outside the target area as needed, making them significant for MR testing.

The existing MR testing methods with spatial selectivity primarily include slice-selective gradient method, saturation pulse method, three-dimensional (3D) spatial selection sequences, and spatially selective radio frequency (RF) pulses. Among them, the slice-selective gradient method selects one or more planes in any orientation through slice-selective gradients. The saturation pulse method achieves arbitrary area selection or suppresses signals from non-target areas using multiple saturation pulses. The 3D spatial selection sequences, such as point-resolved spectroscopy sequence (PRESS) or stimulated echo acquisition mode (STEAM) sequence, can select a cubic area. The spatially selective RF pulses can excite a plane with a local area for target area selection.

However, these implementation methods of spatial selectivity all require the support of a complex gradient system, resulting in high testing costs for the MR system.

SUMMARY

An objective of the present disclosure is to provide a magnetic resonance (MR) system with spatial selectivity and a working method thereof. The present disclosure aims to solve the technical problems that in the prior art the implementation of spatial selectivity requires the support of a complex gradient system, resulting in high testing costs for the MR system.

To achieve the above objective, the present disclosure adopts the following technical solutions:

A first aspect provides an MR system with spatial selectivity, including: a data display and processing module, a spectrometer with at least one transmission channel, at least one power amplifier connected in a one-to-one correspondence to the transmission channel of the spectrometer, a transmit-receive (TR) switch, a preamplifier, multiple sets of coils, and a magnet module, where the data display and processing module is connected to the spectrometer; the spectrometer is separately connected to the at least one power amplifier, the TR switch, and the preamplifier; and the TR switch is separately connected to the preamplifier and a main coil corresponding to a target area;

the spectrometer includes any combination of a single-channel transmission spectrometer and/or a multi-channel transmission spectrometer; when a number of transmission channels of the combined spectrometer is not less than a number of coils, one power amplifier is connected to the TR switch, while other power amplifiers are connected in a one-to-one correspondence to other coils except for the main coil; and when the number of the transmission channels of the combined spectrometer is less than the number of the coils, an output terminal of the at least one power amplifier is connected to at least one power divider, and an output terminal of the at least one power divider is connected to phase shifters corresponding to the number of the coils, where one phase shifter or power amplifier is connected to the TR switch, while remaining phase shifters are connected in a one-to-one correspondence to the other coils except for the main coil; and RF fields and excitation areas generated by each set of coils vary; and a difference between the RF field generated by the main coil corresponding to the target area and the RF fields generated by the other coils is greater than a preset value.

In a possible design, the MR system includes multiple single-channel transmission spectrometers or at least one multi-channel transmission spectrometer, and further includes multiple power amplifiers connected in a one-to-one correspondence to transmission channels; and an output terminal of one of the power amplifiers is connected to the TR switch, while other power amplifiers are connected in a one-to-one correspondence to the other coils except for the main coil.

In a possible design, the MR system includes one single-channel transmission spectrometer or a multi-channel transmission spectrometer with only one transmission channel operating, and further includes a power amplifier connected to the transmission channel; an output terminal of the power amplifier is connected to an input terminal of a power divider; an output terminal of the power divider is connected to multiple phase shifters; and one of the phase shifters is connected to the TR switch, while remaining phase shifters are connected in a one-to-one correspondence to the other coils except for the main coil.

In a possible design, the MR system includes multiple single-channel transmission spectrometers or at least one multi-channel transmission spectrometer, and further includes multiple power amplifiers connected in a one-to-one correspondence to transmission channels; an output terminal of one of the power amplifiers is connected to the TR switch, while other power amplifiers are connected to a power divider; an output terminal of the power divider is connected to multiple phase shifters; and the phase shifters are connected in a one-to-one correspondence to the other coils except for the main coil.

In a possible design, the MR system includes multiple single-channel transmission spectrometers or at least one multi-channel transmission spectrometer, and further includes multiple power amplifiers; an output terminal of each of the power amplifiers is connected to a power divider; an output terminal of each power divider is connected to multiple phase shifters; and one of the phase shifters is connected to the TR switch, while remaining phase shifters are connected in a one-to-one correspondence to the other coils except for the main coil.

In a possible design, the MR system includes two single-channel transmission spectrometers or one multi-channel transmission spectrometer with only two transmission channels operating; and an output terminal of each of the transmission channels is connected to a power amplifier.

A second aspect provides a working method of the MR system with spatial selectivity as described in any possible design of the first aspect, including:

sending, by the data display and processing module, a first instruction to the spectrometer;

controlling, by the spectrometer according to the first instruction, the multiple sets of coils to simultaneously transmit main pulse sequences, through multiple power amplifiers, or controlling the multiple sets of coils to simultaneously transmit the main pulse sequences, through the power amplifier, the power divider, and the phase shifter in sequence, such that a difference between the RF field of a first area and the RF field of the target area is greater than a threshold, where the first area is an overlapping area between the excitation area of the main coil and the excitation areas of the other coils; and sending an MR signal generated in the excitation area of the main coil to the data display and processing module through the TR switch, the preamplifier, and the spectrometer in sequence, achieving spatial selection of the MR signal in the target area.

In a possible design, before the controlling, by the spectrometer according to the first instruction, the multiple sets of coils to simultaneously transmit main pulse sequences, through the multiple power amplifiers, the working method further includes:

sending, by the data display and processing module, a second instruction to the spectrometer, such that the spectrometer controls, according to the second instruction, the other coils except for the main coil to simultaneously transmit identical first saturation pulses, through the multiple power amplifiers, or controls the other coils except for the main coil to simultaneously transmit the identical first saturation pulses, through the power amplifier, the power divider, and the phase shifter in sequence;

where, the first saturation pulses are provided with an adjustable phase and amplitude to maximize saturation of MR signals in the excitation areas of the other coils.

In a possible design, before the controlling, by the spectrometer according to the first instruction, the multiple sets of coils to simultaneously transmit main pulse sequences, through the multiple power amplifiers, the working method further includes:

sending, by the data display and processing module, a third instruction to the spectrometer, such that the spectrometer controls, according to the third instruction, the other coils except for the main coil to transmit different second saturation pulses, through the multiple power amplifiers, or controls the other coils except for the main coil to transmit different second saturation pulses, through the power amplifier, the power divider, and the phase shifter in sequence.

In a possible design, the main pulse sequence includes a Carr-Purcell-Meiboom-Gill (CPMG) sequence.

Compared with the prior art, the present disclosure has the following beneficial effects:

In the present disclosure, the MR RF system includes any combination of a single-channel transmission spectrometer and/or a multi-channel transmission spectrometer, corresponding to a combination of multiple power amplifiers or power amplifiers, power dividers, and phase shifters. Meanwhile, the MR RF system includes multiple sets of coils including a main coil and other coils. Each set of coils corresponds to different RF fields and excitation areas, and the difference between the RF field generated by the main coil corresponding to the target area and the RF field generated by the other coils is greater than a preset value. Thus, when the system is working, according to the need of the target area to be selected, the spectrometer controls multiple sets of coils to simultaneously transmit main pulse sequences through multiple power amplifiers for excitation, or controls multiple sets of coils to simultaneously transmit main pulse sequences through the power amplifier, the power divider, and the phase shifter in sequence for excitation. In this way, the MR signal intensity obtained from different RF fields and excitation areas at the same flip angle varies significantly, thereby achieving spatial selection of MR signals in the target area. The present disclosure improves the accuracy of MR signal testing without the support of a gradient system, reducing the cost and complexity of MR testing.

DETAILED DESCRIPTION OF THE EMBODIMENTS

Figure 1:
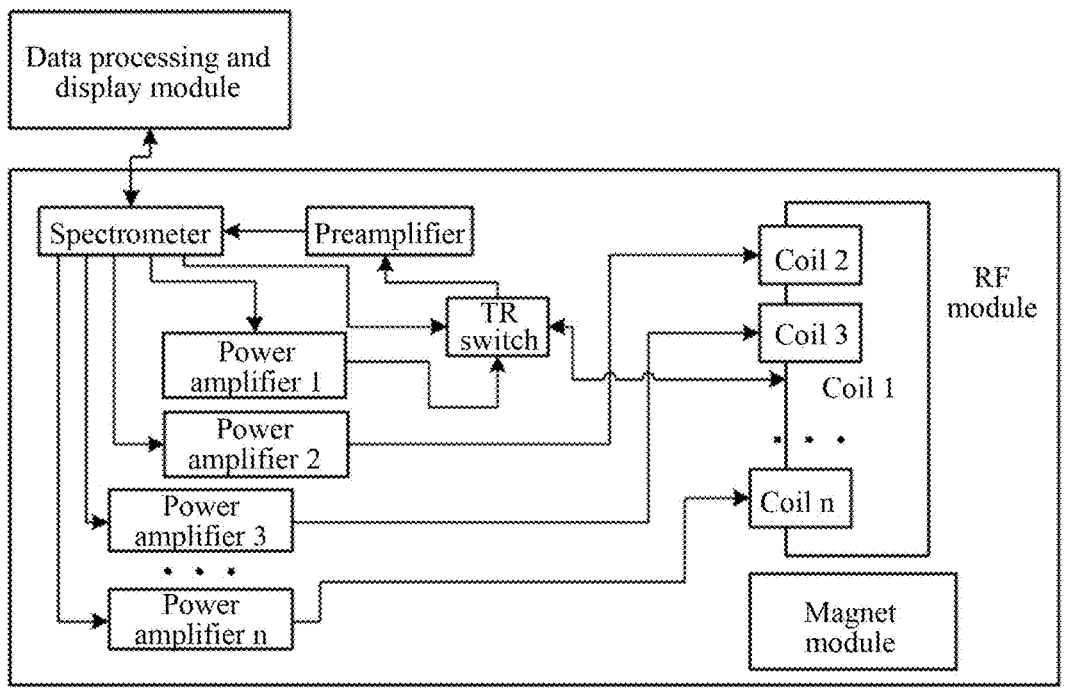
FIG. 1 is a first structural schematic diagram of an MR system with spatial selectivity according to an embodiment of the present disclosure.

To describe the technical solutions in the embodiments of the present disclosure or in the prior art more clearly, the present disclosure is described simply with reference to the drawings and the embodiments or descriptions in the prior art. Apparently, the drawings in the following description show merely some embodiments of the present disclosure, and those skilled in the art may still derive other drawings from these drawings without creative efforts. It should be noted here that the description of these embodiments is used to help understand the present disclosure, but does not constitute a limitation to the present disclosure.

Embodiment

To solve the technical problems that in the prior art the implementation of spatial selectivity requires the support of a complex gradient system, resulting in high testing costs for the MR system, the embodiment of the present disclosure provides an MR system with spatial selectivity. The MR system of the present disclosure can achieve the spatial selection of a target area without the support of a gradient system, lowering the costs and complexity of MR testing.

The MR system with spatial selectivity provided by the embodiment of the present disclosure is described in detail below.

FIGS. 1 to 5 show various structural schematic diagrams of an MR system with spatial selectivity according to an embodiment of the present disclosure. The MR system with spatial selectivity includes: a data display and processing module, a spectrometer with at least one transmission channel, at least one power amplifier connected in a one-to-one correspondence to the transmission channel of the spectrometer, a transmit-receive (TR) switch, a preamplifier, multiple sets of coils, and a magnet module.

The data display and processing module is connected to the spectrometer. The spectrometer is separately connected to the at least one power amplifier, the TR switch, and the preamplifier. The TR switch is separately connected to the preamplifier and a main coil corresponding to a target area.

The spectrometer includes any combination of a single-channel transmission spectrometer and/or a multi-channel transmission spectrometer. When a number of transmission channels of the combined spectrometer is not less than a number of coils, one power amplifier is connected to the TR switch, while other power amplifiers are connected in a one-to-one correspondence to other coils except for the main coil. When the number of the transmission channels of the combined spectrometer is less than the number of the coils, an output terminal of the at least one power amplifier is connected to at least one power divider, and an output terminal of the at least one power divider is connected to phase shifters corresponding to the number of the coils. In this case, one phase shifter or power amplifier is connected to the TR switch, while remaining phase shifters are connected in a one-to-one correspondence to the other coils except for the main coil.

RF fields and excitation areas generated by each set of coils vary; and a difference between the RF field generated by the main coil corresponding to the target area and the RF fields generated by the other coils is greater than a preset value.

The spectrometer, the power amplifier, the TR switch, the preamplifier, the multiple sets of coils, the power divider, the phase shifters, and the magnet module jointly constitute a RF module.

It should be noted that the strength and excitation area of the RF field generated by each coil can be designed according to the requirements of the coil design, including the corresponding winding method, shape, placement position, and/or matching and tuning capacitors on the coil. In this way, the RF fields and excitation areas generated by each set of coils vary, and the difference between the RF field generated by the main coil corresponding to the target area and the RF fields generated by the other coils is greater than the preset value.

It should be noted that the data display and processing module is configured to send an instruction to control a RF pulse sequence and receive an MR signal, so as to complete real-time data processing. The spectrometer is configured to control the RF pulse sequence and receive the MR signal. Each power amplifier includes an input terminal connected to one of the transmission channels of the spectrometer, and is configured to amplify a RF pulse output by the spectrometer. The TR switch is configured to control the transmit-receive switching of a link of the main coil corresponding to the target area. The preamplifier is configured to amplify the received MR signal. The magnet module is configured to generate static magnetic field B0. The multiple sets of RF coil systems are configured to generate multiple RF fields B1 perpendicular to the static magnetic field B0.

It should be noted that in the embodiment of the present disclosure, there are various combinations for the spectrometer, the power amplifier, the power divider, and the phase shifter, including but not limited to the following examples. When the number of the transmission channels of the combined spectrometer is not less than the number of the coils, only multiple power amplifiers connected in a one-to-one correspondence to the transmission channels are provided. Alternatively, when the number of the transmission channels of the combined spectrometer is less than the number of the coils, a combination of the power amplifier, the power divider, and the phase shifter is provided to achieve power division and phase adjustment of the RF pulse. For example, a spectrometer with a single transmission channel corresponds to a single power amplifier, multiple power dividers, multiple phase shifters, and multiple sets of coils; a spectrometer with multiple transmission channels corresponds to multiple power amplifiers, multiple power dividers, multiple phase shifters, and multiple sets of coils; and multiple spectrometers correspond to multiple power amplifiers and power dividers. These combinations are flexible, and will not be elaborated here.

As shown in FIG. 1, in a specific implementation, the MR system includes multiple single-channel transmission spectrometers or at least one multi-channel transmission spectrometer, and further includes multiple power amplifiers connected in a one-to-one correspondence to transmission channels. An output terminal of one of the power amplifiers is connected to the TR switch, while other power amplifiers are connected in a one-to-one correspondence to the other coils except for the main coil.

For example, the entire system includes: a data display and processing module connected to a spectrometer, and configured to send an instruction to control a RF pulse sequence and receive an MR signal, so as to complete real-time data processing; multiple single-channel transmission spectrometers or one multi-channel transmission MR spectrometer configured to control the RF pulse sequence and receive the MR signal; multiple power amplifiers with respective input terminal connected to multiple transmission channels of the spectrometer and respective output terminals connected to the TR switch or multiple RF coils, and configured to amplify the RF pulse output by the spectrometer; the TR switch configured to control the transmit-receive switching of the link of the coil corresponding to the target area; a preamplifier configured to amplify the received MR signal; a magnet module configured to generate static magnetic field B0; and multiple sets of RF coil systems configured to generate multiple RF fields B1 perpendicular to the static magnetic field B0.

Figure 2:
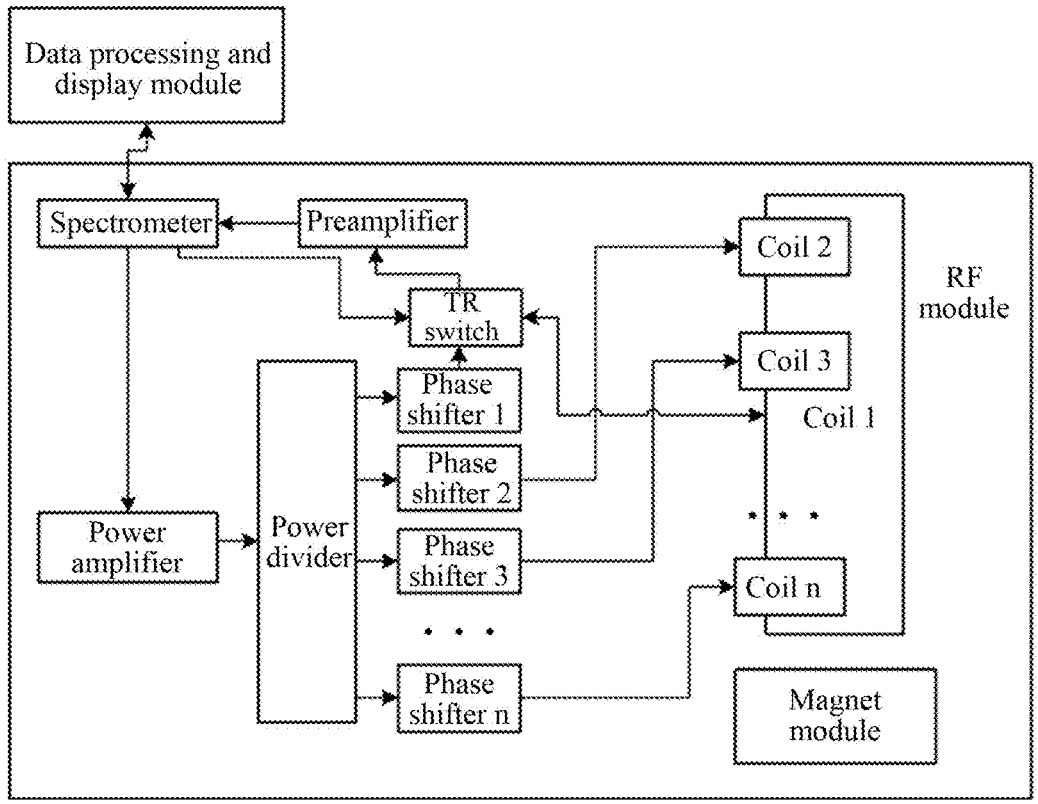
FIG. 2 is a second structural schematic diagram of the MR system with spatial selectivity according to the embodiment of the present disclosure.

As shown in FIG. 2, in a specific implementation, the MR system includes one single-channel transmission spectrometer or a multi-channel transmission spectrometer with only one transmission channel operating, and further includes a power amplifier connected to the transmission channel. An output terminal of the power amplifier is connected to an input terminal of a power divider, and an output terminal of the power divider is connected to multiple phase shifters. One of the phase shifters is connected to the TR switch, while remaining phase shifters are connected in a one-to-one correspondence to the other coils except for the main coil.

For example, the entire system includes: a data display and processing module connected to a spectrometer and configured to send an instruction to control a RF pulse sequence and receive an MR signal, so as to complete real-time data processing; a single-channel transmission MR spectrometer or a multi-channel transmission spectrometer with only one transmission channel operating, configured to control the RF pulse sequence and receive the MR signal; a power amplifier including an input terminal connected to a transmission channel of the spectrometer and an output terminal connected to an input of a multi-way power divider, and configured to amplify the RF pulse output by the spectrometer; the power divider configured to split RF power of an input RF pulse in a single way into multiple ways; multiple phase shifters configured to adjust a phase of the RF pulse in each output way of the power divider; a TR switch configured to control the transmit-receive switching of the link of the coil corresponding to the target area; a preamplifier configured to amplify the received MR signal; a magnet module configured to generate a static magnetic field B0; and multiple sets of RF coil systems configured to generate multiple RF fields B1 perpendicular to the static magnetic field B0. It should be noted that typically, the power amplifier used in a system that includes only one power amplifier needs to provide very high output power to meet the system requirement.

Figure 3:
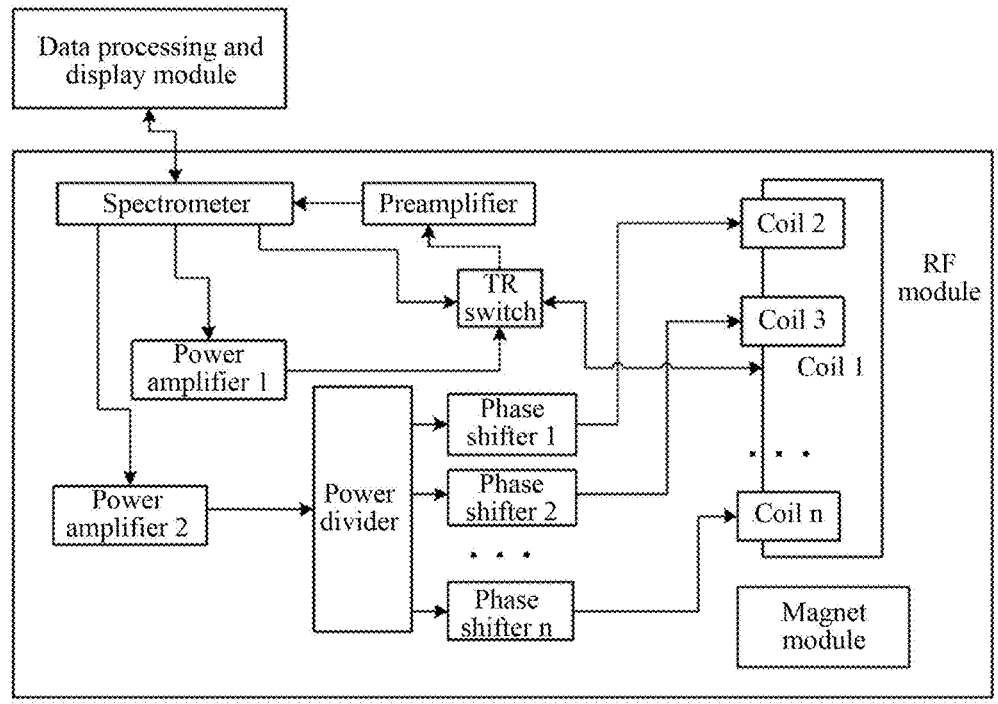
FIG. 3 is a third structural schematic diagram of the MR system with spatial selectivity according to the embodiment of the present disclosure.

As shown in FIG. 3, in a specific implementation, the MR system includes multiple single-channel transmission spectrometers or at least one multi-channel transmission spectrometer. Preferably, the MR system includes two single-channel transmission spectrometers or one multi-channel transmission spectrometer with only two channels operating, and further includes multiple power amplifiers connected in a one-to-one correspondence to transmission channels. An output terminal of one of the power amplifiers is connected to the TR switch, while other power amplifiers are connected to a power divider. An output terminal of the power divider is connected to multiple phase shifters, and the phase shifters are connected in a one-to-one correspondence to the other coils except for the main coil.

For example, the entire system includes: a data display and processing module connected to a spectrometer and configured to send an instruction to control a RF pulse sequence and receive an MR signal, so as to complete real-time data processing; multiple single-channel transmission spectrometers or one multi-channel transmission MR spectrometer configured to control the RF pulse sequence and receive the MR signal; multiple power amplifiers, including one power amplifier with an output terminal connected to the TR switch and other power amplifiers connected to a power divider; multiple power dividers configured to split RF power of the input RF pulse into multiple channels; multiple phase shifters configured to adjust a phase of the RF pulse in each output way of the power divider; a TR switch configured to control the transmit-receive switching of the link of the coil corresponding to the target area; a preamplifier configured to amplify the received MR signal; a magnet module configured to generate a static magnetic field B0; and multiple sets of RF coil systems configured to generate multiple RF fields B1 perpendicular to the static magnetic field B0. Of course, it can be understood that, alternatively, the output terminal of one of the power amplifiers is connected to the TR switch. As for the remaining power amplifiers, some are directly connected to the RF coil, while the rest are first connected to the power divider and the phase shifter and then connected to the RF coil, thereby amplifying the RF pulse output by the spectrometer.

Figure 4:
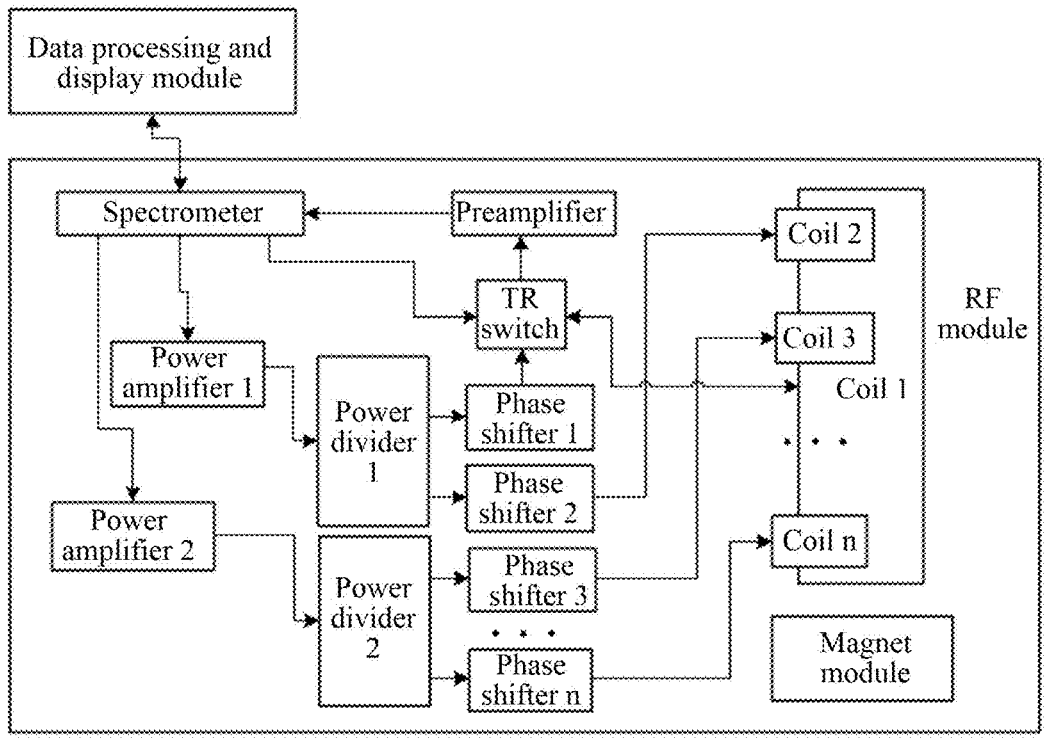
FIG. 4 is a fourth structural schematic diagram of the MR system with spatial selectivity according to the embodiment of the present disclosure.

As shown in FIG. 4, in a specific implementation, the MR system includes multiple single-channel transmission spectrometers or at least one multi-channel transmission spectrometer. Preferably, the MR system includes two single-channel transmission spectrometers or one multi-channel transmission spectrometer with only two transmission channels operating, and further includes multiple power amplifiers. An output terminal of each of the power amplifiers is connected to a power divider, and an output terminal of each power divider is connected to multiple phase shifters. One of the phase shifters is connected to the TR switch, while remaining phase shifters are connected in a one-to-one correspondence to the other coils except for the main coil.

For example, the entire system includes: a data display and processing module connected to a spectrometer and configured to send an instruction to control a RF pulse sequence and receive an MR signal, so as to complete real-time data processing; multiple single-channel transmission spectrometers or one multi-channel transmission MR spectrometer configured to control the RF pulse sequence and receive the MR signal; multiple power amplifiers each connected to a power divider and a phase shifter before being connected to an RF coil, and configured to amplify the RF pulse output by the spectrometer; multiple power dividers configured to split RF power of the input RF pulse into multiple channels; multiple phase shifters configured to adjust a phase of the RF pulse in each output way of the power divider; a TR switch configured to control the transmit-receive switching of the link of the coil corresponding to the target area; a preamplifier configured to amplify the received MR signal; a magnet module configured to generate a static magnetic field B0; and multiple sets of RF coil systems configured to generate multiple RF fields B1 perpendicular to the static magnetic field B0.

Figure 5:
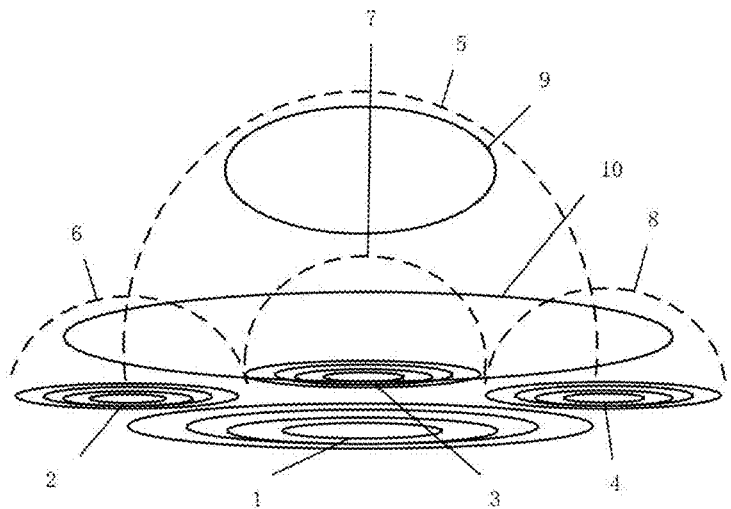
FIG. 5 is a schematic diagram of a type of excitation areas of multiple sets of coils according to the embodiment of the present disclosure.

As shown in FIG. 5, in a specific implementation, each type of MR RF system in the embodiment of the present disclosure includes multiple sets of RF coils, and each set of RF coils correspond to different RF fields and excitation areas. The multiple sets of RF coils perform excitation simultaneously to achieve the purpose of spatial selection. For example, in the FIGS., 1, 2, 3, and 4 respectively represent four different sets of RF coils. 1 represents the main coil, corresponding to the four different excitation areas of 5, 6, 7, and 8. 9 represents a target tissue area for testing, and 10 represents a surrounding tissue area around the target area.

In nuclear magnetic resonance (NMR), under the action of the RF field B1, a macroscopic magnetization vector formed by a spin rotates around the RF field B1. When the macroscopic magnetization vector generated by the spin is rotated 90° by an RF pulse with a certain flip angle (i.e. RF power), a maximum transverse magnetization vector is generated. The transverse magnetization vector is the MR signal.

Therefore, the signal strength is closely related to the RF field B1 and the flip angle of the corresponding RF pulse. If only the main coil 1 shown in the figure is used for excitation, the acquired MR signal will inevitably include a signal from the surrounding tissue 10 in addition to the signal from the target tissue area 9, which will lead to a decrease in testing accuracy. In view of this, this embodiment proposes a working method of the MR system based on the MR system, in order to achieve spatial selection of the target area.

As shown in FIGS. 6 to 9, a second aspect of the embodiment of the present disclosure provides a working method of the MR system with spatial selectivity as described in any possible design of the first aspect, including but not limited to steps S1 to S3.

Step S1. The data display and processing module sends a first instruction to the spectrometer.

Step S2. According to the first instruction, the spectrometer controls the multiple sets of coils to simultaneously transmit main pulse sequences, through the multiple power amplifiers, or controls the multiple sets of coils to simultaneously transmit the main pulse sequences, through the power amplifier, the power divider, and the phase shifter in sequence, such that a difference between the RF field of a first area and the RF field of the target area is greater than a threshold, where the first area is an overlapping area between the excitation area of the main coil and the excitation areas of the other coils.

Figure 6:
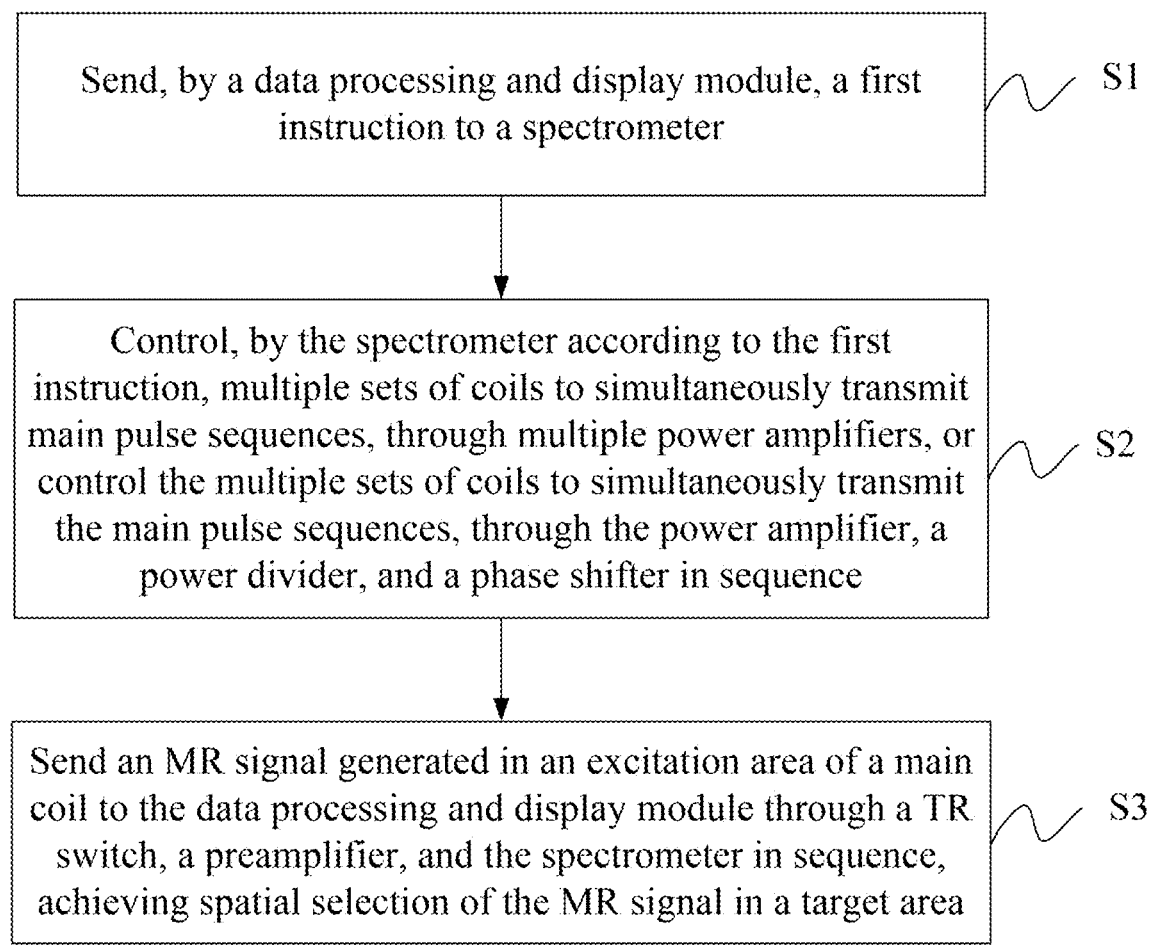
FIG. 6 is a flowchart of a working method of the MR system with spatial selectivity according to the embodiment of the present disclosure.

As shown in FIGS. 4 and 6, when the multiple sets of coils perform transmission simultaneously, a spatially selective RF field is synthesized. The spectrometer controls the amplitude and phase of the transmitted signal through different transmission channels, or controls the phase through the phase shifter. Thus, the RF field in the overlapping area between the main coil 1 and other coils differs greatly from the RF field in the target area, thereby achieving spatial excitation selectivity. For example, the coils 1, 2, 3, and 4 perform excitation simultaneously. In this case, when the macroscopic magnetization vector generated by a spin in the excitation area of the coil 1 is rotated 90°, due to the significant difference between the RF field generated by the coils 2, 3, and 4 and the RF field generated by the coil 1, the macroscopic magnetization vector generated by a spin in the excitation areas of the coils 2, 3, and 4 is not rotated 90° or far exceeds 90°, resulting in a low signal. Except for the overlapping area between the excitation area of the coil 1 and the excitation areas of the coils 2, 3, and 4, an area (i.e. the target area) in the excitation area of the coil presents a high signal, which means that the target tissue area presents a high signal, thereby achieving the purpose of spatial selection.

As shown in FIG. 6, specifically, the coils 1 to n simultaneously transmit the main pulse sequences. The main pulse sequence is any RF pulse that can excite to generate the MR signal, including but not limited to a Carr-Purcell-Meiboom-Gill (CPMG) pulse sequence. In NMR, under the action of the RF field B1, the macroscopic magnetization vector formed by the spin rotates around the RF field B1. The macroscopic magnetization vector generated by the spin is rotated 90° through a RF pulse with a certain flip angle to generate a maximum transverse magnetization vector. In order to achieve the purpose of spatial selection, there is a significant difference between the RF field B1 generated by the coil 1 and the RF field B1 generated by the coils 2 to n. All the coils are excited by RF pulses with the same flip angle. The flip angle of the RF pulse satisfies a flip angle corresponding to the RF field B1 generated by the coil 1, that is, a high signal is present in the excitation area of the coil 1, while a low signal is present in the excitation areas of the coils 2 to n. The target area of interest is a part of the excitation area of the coil 1 except for the excitation areas of the coils 2 to n. The MR signal from the excitation area of the coil 1 is received. The part of the excitation area of the coil 1 except for the excitation areas of the coil 2 to n presents a high signal, while the overlapping area between the excitation area of the coil 1 and the excitation areas of the coils 2 to n presents a low signal, thereby achieving spatial selection.

Figure 7:
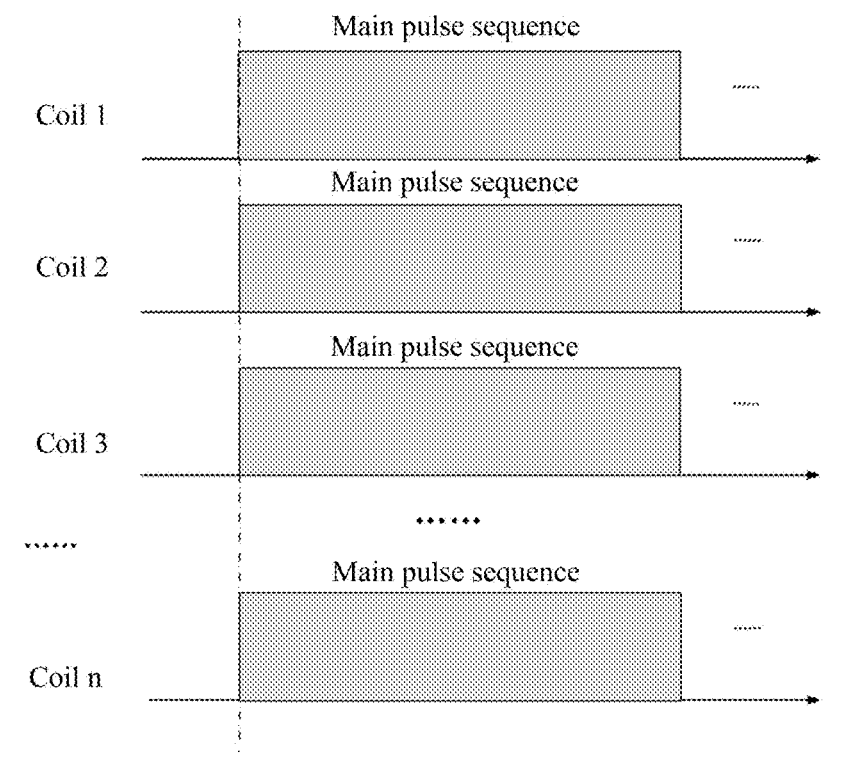
FIG. 7 is a schematic diagram of a first type of pulse sequences of the multiple sets of coils according to the embodiment of the present disclosure.

As shown in FIG. 7, in a specific implementation, in order to achieve a better spatial selection effect, the working method further includes the following step before the spectrometer controls the multiple sets of coils to simultaneously transmit the main pulse sequences through the multiple power amplifiers according to the first instruction.

The data display and processing module sends a second instruction to the spectrometer, such that the spectrometer controls, according to the second instruction, the other coils except for the main coil to simultaneously transmit identical first saturation pulses, through the multiple power amplifiers, or controls the other coils except for the main coil to simultaneously transmit the identical first saturation pulses, through the power amplifier, the power divider, and the phase shifter in sequence.

The first saturation pulses are provided with an adjustable phase and amplitude to maximize saturation of MR signals in the excitation areas of the other coils.

Specifically, the coils 2 to n first transmit the identical saturation pulses simultaneously, and then all the coils transmit the main pulse sequences of the RF pulses with the same flip angle. The flip angle of the RF pulse satisfies the flip angle corresponding to the RF field B1 generated by the coil 1. The excitation area of the coil 1 presents a high signal, while the excitation areas of the coils 2 to n present no signal. The target area of interest is a part of the excitation area of the coil 1 except for the excitation areas of the coils 2 to n. The MR signal from the excitation area of the coil 1 is received. The part of the excitation area of the coil 1 except for the excitation areas of the coils 2 to n presents a high signal, while the overlapping area between the excitation area of the coil 1 and the excitation areas of the coils 2 to n presents no signal, thereby achieving spatial selection effect.

Figure 8:
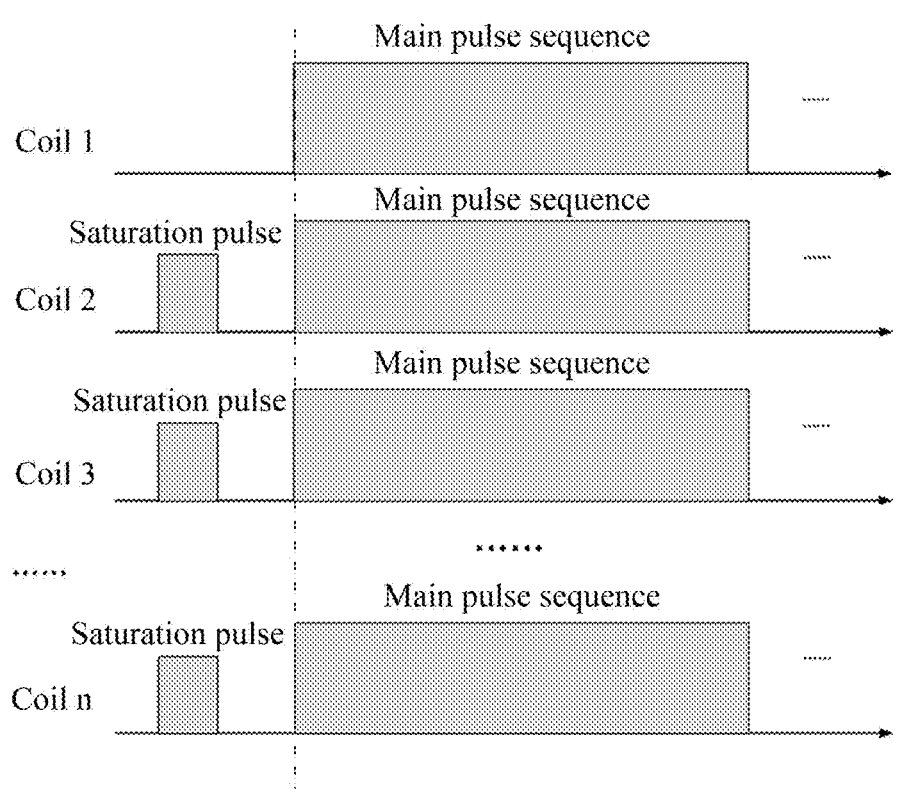
FIG. 8 is a schematic diagram of a second type of pulse sequences of the multiple sets of coils according to the embodiment of the present disclosure.
Figure 9:
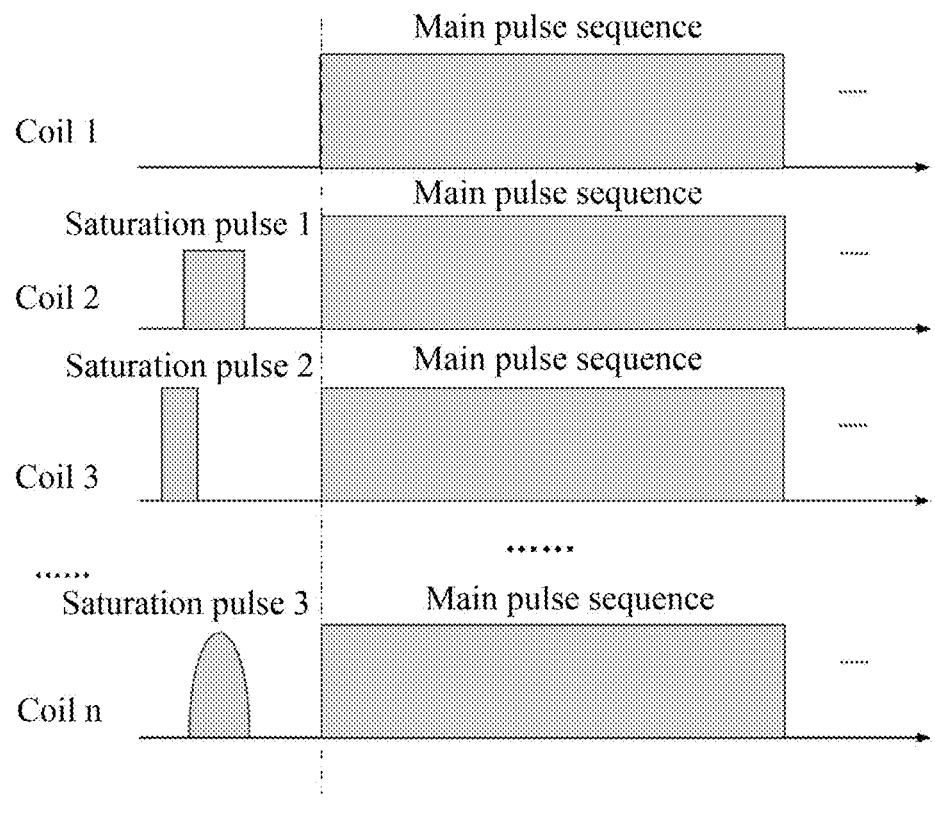
FIG. 9 is a schematic diagram of a third type of pulse sequences of the multiple sets of coils according to the embodiment of the present disclosure.

As shown in FIG. 8, in a specific implementation, in order to further achieve a better spatial selection effect, the working method further includes the following step before the spectrometer controls the multiple sets of coils to simultaneously transmit the main pulse sequences through the multiple power amplifiers according to the first instruction.

The data display and processing module sends a third instruction to the spectrometer, such that the spectrometer controls, according to the third instruction, the other coils except for the main coil to transmit different second saturation pulses, through the multiple power amplifiers, or controls the other coils except for the main coil to transmit different second saturation pulses, through the power amplifier, the power divider, and the phase shifter in sequence.

Specifically, each of the coils 2 to n can choose different saturation pulses according to the actual situation, which can have different flip angles or shapes. All the coils transmit the main pulse sequences of the RF pulses with the same flip angle. The flip angle of the RF pulse satisfies the flip angle corresponding to the RF field B1 generated by the coil 1. The excitation area of the coil 1 presents a high signal, while the excitation areas of the coils 2 to n present no signal. The target area of interest is a part of the excitation area of the coil 1 except for the excitation areas of the coils 2 to n. The MR signal from the excitation area of the coil 1 is received. The part of the excitation area of the coil 1 except for the excitation areas of the coils 2 to n presents a high signal, while the overlapping area between the excitation area of the coil 1 and the excitation areas of the coils 2 to n presents no signal, thereby achieving spatial selection effect.

Step S3. An MR signal generated in the excitation area of the main coil is sent to the data display and processing module through the TR switch, the preamplifier, and the spectrometer in sequence, achieving spatial selection of the MR signal in the target area.

Based on the above disclosed content, in the embodiment of the present disclosure, the MR RF system includes any combination of a single-channel transmission spectrometer and/or a multi-channel transmission spectrometer, corresponding to a combination of multiple power amplifiers or power amplifiers, power dividers, and phase shifters. Meanwhile, the MR RF system includes multiple sets of coils including a main coil and other coils. Each set of coils corresponds to different RF fields and excitation areas, and the difference between the RF field generated by the main coil corresponding to the target area and the RF field generated by the other coils is greater than a preset value. Thus, when the system is working, according to the need of the target area to be selected, the spectrometer controls multiple sets of coils to simultaneously transmit main pulse sequences through multiple power amplifiers for excitation, or controls multiple sets of coils to simultaneously transmit main pulse sequences through the power amplifier, the power divider, and the phase shifter in sequence for excitation. In this way, the MR signal intensity obtained from different RF fields and excitation areas at the same flip angle varies significantly, thereby achieving spatial selection of MR signals in the target area. The present disclosure improves the accuracy of MR signal testing without the support of a gradient system, reducing the cost and complexity of MR testing.

Validation Example

In order to validate the spatial selectivity of the MR system and its working method proposed in the embodiment of the present disclosure, an experimental example is proposed to illustrate the feasibility of the system and its working method, specifically as follows.

Figure 10:
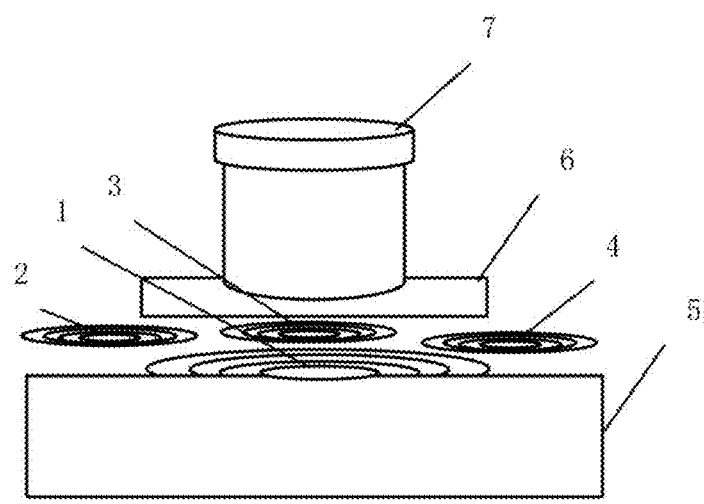
FIG. 10 is a structural schematic diagram of phantom excitation in an experimental example according to the embodiment of the present disclosure.

FIG. 10 is a schematic diagram showing the relative positions of the magnet module, the coil module, and a measurement module in the MR system with spatial selectivity. In the FIG., 1 represents the main coil, corresponding to a large excitation area with an excitation depth of 8 cm. Coils 2, 3, and 4 correspond to small excitation areas with an excitation depth of 3.5 cm, and are located on magnet 5. A surface of the coils is provided with 3 cm thick rectangular oil phantom 6 and cylindrical oil phantom 7 with a diameter of 8 cm and a height of 12 cm.

Specifically, this verification example uses the system shown in FIG. 4, which includes a dual-channel transmission spectrometer, two power amplifiers, and two two-way power dividers. The main pulse sequence is a CPMG sequence for measuring a signal-to-noise ratio (SNR). The following experiments were conducted.

Experiment 1: All coils simultaneously transmitted the main pulse sequences.

When only a shallow oil pad was placed, the SNR was measured as 4.

When a deep oil phantom was placed on the shallow oil pad, the SNR was measured as 14.

When the shallow oil pad was replaced with a dry wooden board of the same thickness, while the deep oil pad was kept in its original spatial position, the measured SNR was measured as 14.

Experiment 2: Coils 2, 3, and 4 first simultaneously transmitted identical saturation pulses, and then all the coils simultaneously transmitted main pulse sequences.

When only a shallow oil pad was placed, the SNR was measured as 2.

When a deep oil phantom was placed on the shallow oil pad, the SNR was measured as 16.

When the shallow oil pad was replaced with a dry wooden board of the same thickness, while the deep oil pad was kept in its original spatial position, the measured SNR was measured as 16.

Experiment 3: Coils 2, 3, and 4 first transmitted different saturation pulses at different times, and then all the coils simultaneously transmitted main pulse sequences.

When only a shallow oil pad was placed, the SNR was measured as 0.8.

When a deep oil phantom was placed on the shallow oil pad, the SNR was measured as 16.

When the shallow oil pad was replaced with a dry wooden board of the same thickness, while the deep oil pad was kept in its original spatial position, the measured SNR was measured as 16.

From the results of Experiments 1 to 3, it can be seen that the SNR was very low when only the shallow oil model was placed, indicating that the MR signal in the area where the shallow oil model was located was very low. When the deep oil phantom was placed, regardless of whether the shallow oil phantom was placed or not, the SNR remained basically unchanged, indicating that the excitation area of the main coil 1 was basically unaffected except for the excitation areas of other coils. Therefore, the system and working method proposed in the embodiments of the present disclosure have good spatial selectivity.

Finally, it should be noted that the above described are only preferred embodiments of the present disclosure and are not intended to limit the present disclosure. Any modification, equivalent substitution, improvement, etc. within the spirit and principles of the present disclosure shall fall within the scope of protection of the present disclosure.

The invention claimed is:

1. A magnetic resonance (MR) system with spatial selectivity, comprising: a data display and processing module, a spectrometer with at least one transmission channel, at least one power amplifier connected in a one-to-one correspondence to the transmission channel of the spectrometer, a transmit-receive (TR) switch, a preamplifier, a plurality of sets of coils, and a magnet module, wherein the data display and processing module is connected to the spectrometer; the spectrometer is separately connected to the at least one power amplifier, the TR switch, and the preamplifier; and the TR switch is separately connected to the preamplifier and a main coil corresponding to a target area;

the spectrometer comprises any combination of a single-channel transmission spectrometer and/or a multi-channel transmission spectrometer; when a number of transmission channels of the combined spectrometer is greater than or equal to a number of coils, one power amplifier is connected to the TR switch, while other power amplifiers are connected in a one-to-one correspondence to other coils except for the main coil; and when the number of the transmission channels of the combined spectrometer is less than the number of the coils, an output terminal of the at least one power amplifier is connected to at least one power divider, and an output terminal of the at least one power divider is connected to phase shifters corresponding to the number of the coils, wherein one phase shifter or power amplifier is connected to the TR switch, while remaining phase shifters are connected in a one-to-one correspondence to the other coils except for the main coil; and radio frequency (RF) fields and excitation areas generated by each set of coils vary; and a difference between the RF field generated by the main coil corresponding to the target area and the RF fields generated by the other coils is greater than a preset value.

2. The MR system with the spatial selectivity according to claim 1, wherein the MR system comprises a plurality of single-channel transmission spectrometers or at least one multi-channel transmission spectrometer, and further comprises a plurality of power amplifiers connected in a one-to-one correspondence to transmission channels; and an output terminal of one of the plurality of power amplifiers is connected to the TR switch, while other power amplifiers are connected in a one-to-one correspondence to the other coils except for the main coil.

3. The MR system with the spatial selectivity according to claim 1, wherein the MR system comprises one single-channel transmission spectrometer or a multi-channel transmission spectrometer with only one transmission channel operating, and further comprises a power amplifier connected to the transmission channel; an output terminal of the power amplifier is connected to an input terminal of a power divider; an output terminal of the power divider is connected to a plurality of phase shifters; and one of the phase shifters is connected to the TR switch, while remaining phase shifters are connected in a one-to-one correspondence to the other coils except for the main coil.

4. The MR system with the spatial selectivity according to claim 1, wherein the MR system comprises a plurality of single-channel transmission spectrometers or at least one multi-channel transmission spectrometer, and further comprises a plurality of power amplifiers connected in a one-to-one correspondence to transmission channels; an output terminal of one of the plurality of power amplifiers is connected to the TR switch, while other power amplifiers are connected to a power divider; an output terminal of the power divider is connected to a plurality of phase shifters; and the phase shifters are connected in a one-to-one correspondence to the other coils except for the main coil.

5. The MR system with the spatial selectivity according to claim 1, wherein the MR system comprises a plurality of single-channel transmission spectrometers or at least one multi-channel transmission spectrometer, and further comprises a plurality of power amplifiers; an output terminal of each of the plurality of power amplifiers is connected to a power divider; an output terminal of each power divider is connected to a plurality of phase shifters; and one of the phase shifters is connected to the TR switch, while remaining phase shifters are connected in a one-to-one correspondence to the other coils except for the main coil.

6. A working method of the MR system with the spatial selectivity according to claim 1, comprising following steps:
sending, by the data display and processing module, a first instruction to the spectrometer;
controlling, by the spectrometer according to the first instruction, the plurality of sets of coils to simultaneously transmit main pulse sequences, through a plurality of power amplifiers, or controlling the plurality of sets of coils to simultaneously transmit the main pulse sequences, through the power amplifier, the power divider, and the phase shifter in sequence, wherein a difference between the RF field of a first area and the RF field of the target area is greater than a threshold, wherein the first area is an overlapping area between the excitation area of the main coil and the excitation areas of the other coils; and
sending an MR signal generated in the excitation area of the main coil to the data display and processing module through the TR switch, the preamplifier, and the spectrometer in sequence, achieving spatial selection of the MR signal in the target area.

7. The MR system with the spatial selectivity according to claim 4, wherein the MR system comprises two single-channel transmission spectrometers or one multi-channel transmission spectrometer with only two transmission channels operating; and an output terminal of each of the transmission channels is connected to a power amplifier.

8. The working method according to claim 6, wherein before the step of controlling, by the spectrometer according to the first instruction, the plurality of sets of coils to simultaneously transmit main pulse sequences, through the plurality of power amplifiers, the working method further comprises:
sending, by the data display and processing module, a second instruction to the spectrometer, wherein the spectrometer controls, according to the second instruction, the other coils except for the main coil to simultaneously transmit identical first saturation pulses, through the plurality of power amplifiers, or controls the other coils except for the main coil to simultaneously transmit the identical first saturation pulses, through the power amplifier, the power divider, and the phase shifter in sequence;
wherein, the first saturation pulses are provided with an adjustable phase and amplitude to maximize saturation of MR signals in the excitation areas of the other coils.

9. The working method according to claim 6, wherein before the step of controlling, by the spectrometer according to the first instruction, the plurality of sets of coils to simultaneously transmit main pulse sequences, through the plurality of power amplifiers, the working method further comprises:
sending, by the data display and processing module, a third instruction to the spectrometer, wherein the spectrometer controls, according to the third instruction, the other coils except for the main coil to transmit different second saturation pulses, through the plurality of power amplifiers, or controls the other coils except for the main coil to transmit different second saturation pulses, through the power amplifier, the power divider, and the phase shifter in sequence.

10. The working method according to claim 6, wherein the main pulse sequence comprises a Carr-Purcell-Meiboom-Gill (CPMG) sequence.

11. The MR system with the spatial selectivity according to claim 5, wherein the MR system comprises two single-channel transmission spectrometers or one multi-channel transmission spectrometer with only two transmission channels operating; and an output terminal of each of the transmission channels is connected to a power amplifier.

12. The working method according to claim 6, wherein the MR system comprises a plurality of single-channel transmission spectrometers or at least one multi-channel transmission spectrometer, and further comprises a plurality of power amplifiers connected in a one-to-one correspondence to transmission channels; and an output terminal of one of the plurality of power amplifiers is connected to the TR switch, while other power amplifiers are connected in a one-to-one correspondence to the other coils except for the main coil.

13. The working method according to claim 6, wherein the MR system comprises one single-channel transmission spectrometer or a multi-channel transmission spectrometer with only one transmission channel operating, and further comprises a power amplifier connected to the transmission channel; an output terminal of the power amplifier is connected to an input terminal of a power divider; an output terminal of the power divider is connected to a plurality of phase shifters; and one of the phase shifters is connected to the TR switch, while remaining phase shifters are connected in a one-to-one correspondence to the other coils except for the main coil.

14. The working method according to claim 6, wherein the MR system comprises a plurality of single-channel transmission spectrometers or at least one multi-channel transmission spectrometer, and further comprises a plurality of power amplifiers connected in a one-to-one correspondence to transmission channels; an output terminal of one of the plurality of power amplifiers is connected to the TR switch, while other power amplifiers are connected to a power divider; an output terminal of the power divider is connected to a plurality of phase shifters; and the phase shifters are connected in a one-to-one correspondence to the other coils except for the main coil.

15. The working method according to claim 6, wherein the MR system comprises a plurality of single-channel transmission spectrometers or at least one multi-channel transmission spectrometer, and further comprises a plurality of power amplifiers; an output terminal of each of the plurality of power amplifiers is connected to a power divider; an output terminal of each power divider is connected to a plurality of phase shifters; and one of the phase shifters is connected to the TR switch, while remaining phase shifters are connected in a one-to-one correspondence to the other coils except for the main coil.

16. The working method according to claim 14, wherein the MR system comprises two single-channel transmission spectrometers or one multi-channel transmission spectrometer with only two transmission channels operating; and an output terminal of each of the transmission channels is connected to a power amplifier.

17. The working method according to claim 15, wherein the MR system comprises two single-channel transmission spectrometers or one multi-channel transmission spectrometer with only two transmission channels operating; and an output terminal of each of the transmission channels is connected to a power amplifier.

18. The working method according to claim 12, wherein before the step of controlling, by the spectrometer according to the first instruction, the plurality of sets of coils to simultaneously transmit main pulse sequences, through the plurality of power amplifiers, the working method further comprises:
sending, by the data display and processing module, a second instruction to the spectrometer, wherein the spectrometer controls, according to the second instruction, the other coils except for the main coil to simultaneously transmit identical first saturation pulses, through the plurality of power amplifiers, or controls the other coils except for the main coil to simultaneously transmit the identical first saturation pulses, through the power amplifier, the power divider, and the phase shifter in sequence;
wherein, the first saturation pulses are provided with an adjustable phase and amplitude to maximize saturation of MR signals in the excitation areas of the other coils.

19. The working method according to claim 13, wherein before the step of controlling, by the spectrometer according to the first instruction, the plurality of sets of coils to simultaneously transmit main pulse sequences, through the plurality of power amplifiers, the working method further comprises:
sending, by the data display and processing module, a second instruction to the spectrometer, wherein the spectrometer controls, according to the second instruction, the other coils except for the main coil to simultaneously transmit identical first saturation pulses, through the plurality of power amplifiers, or controls the other coils except for the main coil to simultaneously transmit the identical first saturation pulses, through the power amplifier, the power divider, and the phase shifter in sequence;
wherein, the first saturation pulses are provided with an adjustable phase and amplitude to maximize saturation of MR signals in the excitation areas of the other coils.

20. The working method according to claim 14, wherein before the step of controlling, by the spectrometer according to the first instruction, the plurality of sets of coils to simultaneously transmit main pulse sequences, through the plurality of power amplifiers, the working method further comprises:
sending, by the data display and processing module, a second instruction to the spectrometer, wherein the spectrometer controls, according to the second instruction, the other coils except for the main coil to simultaneously transmit identical first saturation pulses, through the plurality of power amplifiers, or controls the other coils except for the main coil to simultaneously transmit the identical first saturation pulses, through the power amplifier, the power divider, and the phase shifter in sequence;
wherein, the first saturation pulses are provided with an adjustable phase and amplitude to maximize saturation of MR signals in the excitation areas of the other coils.

* * * * *